United States Patent [19]

Shikita et al.

[11] 4,293,540

[45] Oct. 6, 1981

[54] GRANULAR CERAMIC CARRIER FOR ADMINISTRATION OF MEDICINES AND MEDICINE SUPPORTED THEREIN

[75] Inventors: Takuji Shikita, Matsubara; Masaya Hirabayashi, Yokaichi, both of Japan

[73] Assignee: Kyoto Ceramic Co., Ltd., Kyoto, Japan

[21] Appl. No.: 120,916

[22] Filed: Feb. 12, 1980

[30] Foreign Application Priority Data

Feb. 13, 1979 [JP] Japan .................................. 54-15917

[51] Int. Cl.$^3$ ....................... A61K 9/22; A61K 33/08; A61J 3/00; A61J 3/10
[52] U.S. Cl. ........................................ 424/26; 424/19; 424/23; 424/157; 424/16
[58] Field of Search ...................... 424/19, 26, 157, 23

[56] References Cited

U.S. PATENT DOCUMENTS 3,923,969  12/1975  Boukol et al. ........................ 424/23

OTHER PUBLICATIONS

Chem. Abst., vol. 82-1975-144919x.

*Primary Examiner*—Stanley J. Friedman

[57] ABSTRACT

Disclosed is a carrier for administration of medicines, which consists of a granular shaped article of a porous ceramic material having communicating fine pores. Pores of this carrier are impregnated with a medicine, or a capsule is formed from this carrier and the inner space of the carrier is filled with a medicine. In the resulting impregnated carrier or filled capsule, a desirable property of gradually releasing the medicine is obtained and a good durability of the effect of the medicine can be attained.

3 Claims, 5 Drawing Figures

GRANULAR CERAMIC CARRIER FOR ADMINISTRATION OF MEDICINES AND MEDICINE SUPPORTED THEREIN

BACKGROUND OF THE INVENTION (1) Field of the Invention:

The present invention relates to a ceramic carrier for administration of medicines, which consists of a small granule of a porous ceramic material.

(2) Description of the Prior Art:

Oral administration, external application and injection into muscles, blood vessels and the like have heretofore been adopted as means for administration of medicines into living bodies.

However, when an antibiotic substance is used for preventing suppuration in an incised part, a medicine absorbed passes through all the parts of a living body inclusive of the incised part. In other words, although only a part of a living body requires a medicine, the medicine passes throughout the body and the medicinal effect of the medicine is substantially consumed in normal parts not requiring the medicine. Accordingly, it is difficult to maintain a therapeutic effect for a long time continuously, and in order to obtain a durable effect, the medicine should be administered continuously. This often results in production of undesirable side effects.

In order to overcome this disadvantage, it is most desired to administer a medicine only to a limited part of a living body truly requiring a therapeutic effect and appropriately adjust the duration of the effect of the medicine according to the condition and kind of the disease.

It is known that when a medicine is supported on an appropriate carrier, a gradual release characteristic can be obtained. For example, German Patent Application Laid-Open Specifications No. 2,651,441.0 and No. 2,727,535.0 teach that when an antibiotic substance such as Gentamicin is supported on a granule of a polymethacrylate or polyacrylate, a gradual release characteristic of the active ingredient can be obtained.

According to the teachings of these prior art references, a granule is prepared from a pasty composition comprising the above-mentioned polymer, a medicine, a monomer and a polymerization catalyst, and the resulting granule should be cured. Accordingly, the preparation procedures are complicated and troublesome. Furthermore, in this conventional process, it is very difficult to control the speed of releasing the medicine. Moreover, it is apprehended that the polymerization catalyst (radical initiator) has undesirable effects on the medicine. Still further, the polymer acting as the carrier is poor in the affinity with a living body, and causes harm to the living body. Accordingly, the granular supported medicine applied for remedy of such disease as the osteomyelitis should be taken out from the body after recovery.

SUMMARY OF THE INVENTION

We found that a granular shaped article of a porous ceramic material having communication pores is used as a carrier for a medicine, a good gradual release characteristic of the medicine can be obtained and the effect of the medicine can be exerted durably for a long time, and this carrier does no harm to a living body and is excellent in the affinity with the living body. Therefore, various advantages can be attained, when this granular porous carrier is used.

More specifically, in accordance with the present invention, there is provided a granular ceramic carrier for administration of medicines, which consists of a granular shaped article of a porous ceramic material having a maximum size not larger than 20 mm, said porous ceramic material including communication pores.

This granular carrier may be used in the form having a solid core or in the form of a hollow capsule. A medicine is packed in fine pores of the granule or in the inner space in case of a capsule by impregnation or filling, and the packed medicine can be administered and used for remedy of various diseases.

A ceramic material, especially an alumina ceramic material, is excellent in the strength and the physical and chemical stability and also in the affinity with a living body, and when this ceramic material is used for the above-mentioned purposes, various disadvantages caused by the use of conventional resinous carriers can be eliminated effectively.

Furthermore, in this ceramic carrier, the medicine release characteristic can be changed in a considerably broad range by controlling the pore size and porosity (the ratio of the pore volume to the total volume of the granule). This is one of prominent advantages that can be attained by the present invention.

The porous ceramic material is preferably composed of a fired body of α-alumina, but it may be composed of a fired body of apatite as described hereinafter.

It is preferred that the maximum size of the porous granule be in the range of from 0.1 to 20 mm, particularly from 1 to 10 mm. It also is preferred that the average pore size be in the range of from 1 to 200 microns, particularly from 5 to 100 microns, and that the porosity be in the range of from 5 to 50%, particularly 20 to 40%.

DETAILED DESCRIPTION OF THE PREFERRED EMBODIMENTS

The present invention will now be described in detail with reference to the accompanying drawings.

Figure 1:
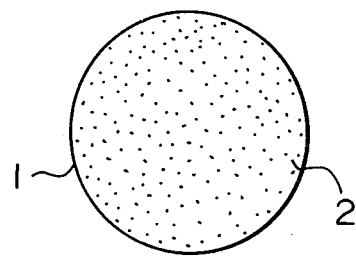
FIG. 1 is a sectional view illustrating one embodiment of the small granule according to the present invention.

Referring to FIG. 1 illustrating one embodiment of the present invention, a small granule 1 is composed of a porous ceramic material and this small granule 1 has a great number of pores 2 irregular in the shape. The outer shape of the small granule 1 is not particularly critical, but it may have a spherical shape, an elliptical shape, a corner-rounded cubic shape or a bean-like shape. An optimum shape is selected according to the intended use. The outer size of the small granule is changed according to the application place, but when the small granule is applied to a human body as a living body, the size of the maximum diameter portion is ordinarily adjusted to less than 2 cm and particularly to less than 1 cm. A great number of pores 2 obtained in a porous ceramic material constituting the small granule 1 are communicating with one another, and the size and porosity of the pores 2 may be changed in broad ranges.

As the method for preparing this porous ceramic material, there can be mentioned (1) a method in which calcination is stopped before completion of sintering, (2) a method in which calcination is carried out in the presence of a combustible or evaporable substance and (3) a method in which ceramic particles uniform in the size are bonded by calcination. When the small ceramic granule of the present invention is used for administration of medicines, it is preferred that the pore size be not larger than about 200μ, especially not larger than 100μ, though the preferred pore size differs to some extent depending on the kind of the medicine to be supported. When the same medicine is supported in the same amount, the duration time of the effect is changed according to the size and number of the pores 2, that is, the porosity of the pores 2. Therefore, in the small granule 1, the porosity of the pores 2 is adjusted so that a duration period of the effect of the medicine optimum to the disease can be obtained. For example, in case of a medicine required to exert a therapeutic effect continuously for a long time, such as a carcinostatic agent, insuline or a hormone, the amount of the medicine is determined according to the disease condition, and the porosity of the small granule 1 is appropriately reduced.

Figure 2A:
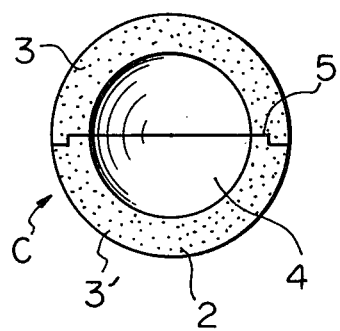
FIGS. 2-A and 2-B are sectional views illustrating another embodiments (capsules) of the small granule according to the present invention.
Figure 2B:
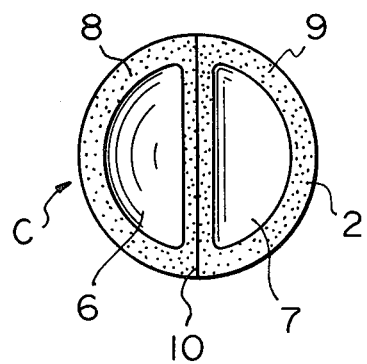

In the foregoing embodiment, the medicine is supported in pores 2 of the small granule 1. In the present invention, however, the manner of supporting medicines is not limited to one illustrated in the foregoing embodiment but various other methods may be adopted. For example, as shown in FIG. 2-A, a small granule is formed by bonding two semi-spheres 3 formed of a porous ceramic material at a bonding portion 5 to form a capsule C, and a medicine is packed in an inner space 4 of the capsule 4. The inner space 4 of the capsule C may be divided into a plurality of parts according to need. Furthermore, as shown in FIG. 2-B, a small granule consists of a capsule C of a porous ceramic material having two semi-spherical inner spaces 6 and 7 bonded together at a bonding portion 10, and different kinds of medicines may be packed in these inner spaces 6 and 7, respectively. Any of liquid, powdery and jellied medicines may be packed in such capsule composed of a porous ceramic material. When a liquid medicine is packed in such capsule, the duration time of the effect is relatively short and is ordinarily shorter than 10 hours. Accordingly, it is preferred that a powdery or jellied medicine be supported in such capsule. In case of a powdery medicine, it is possible to maintain the effect for such a long time as several years by supporting the powdery medicine in the capsule so that the medicine is very gradually dissolved out by the body fluid.

A bead-like or capsular small granule composed of a porous ceramic material, which includes a medicine supported in the interior pores or the inner spaces of the capsule, is administered into a living body, and the supported medicine is gradually dissolved out by the body fluid such as gastric juice, and the medicine exterts a medicinal effect in the stomach or the intestines and is then discharged from the living body. In order to prevent infection with *Pseudomonas pyocyaneum, Staphylococcus aureus* and the like bacteria and to cure diseases caused by these bacteria, a small granule containing a Cephalosporin medicine supported in the interior pores or the inner spaces of the capsule is inserted in the muscle, whereby the intended effect can be attained. After recovery, the inserted small ceramic granule may be taken out, and even if the inserted small ceramic granule is left in the muscle, no bad influences are imposed on the living body because it is harmless.

For remedy of the osteomyelitis, a necessary number of small ceramic granules containing a predetermined medicine supported therein are applied into the medulla. The medicine is gradually released from the small granules to cure the osteomyelitis. Even if the small granules are left in the medulla after remedy of the disease, no bad influences are imposed on the living body. In the treatment of the bone tumor, a small ceramic granule containing a carcinostatic agent supported therein is packed in a bone-cut-out portion, whereby regeneration of the tumor tissue can be controlled for a long time while promoting the growth and propagation of the bone in this bone-cut-out portion.

In this case, in order to further promote the growth and propagation of the bone, a small granule formed of a porous ceramic material of apatite having a composition quite close to that of the bone may be used.

The granular ceramic carrier of the present invention is especially valuable as a carrier for antibiotics. For example, the granular ceramic carrier of the present invention is advantageously used for supporting Erythromycin, Lincomycin, Clindamycin, Novobiocin, Vancomycin, fusidic acid, Rifamycin, Neomycin, Kanamycin, Gentamicin, penicillins and Cephalosporins.

The medicine may be packed in the granular ceramic carrier of the present invention in an amount, at the maximum, corresponding to the porosity or the inner space in case of the capsule. Ordinarily, however, it is preferred that the medicine be supported in an amount of 0.1 to 30% by weight, particularly 1 to 15% by weight, based on the carrier.

The medicine-administering agent of the present invention comprises an antibiotic such as mentioned above, especially Gentamicin, supported in a small granule of a porous ceramic material, such as mentioned above, and this medicine-administering agent is especially valuably used for remedy of the osteomyelitis by embedding the agent in the affected bone texture or the vicinity thereof.

The relation among the kind of the medicine supported into the pores or the inner space of the capsule in the granular ceramic carrier of the present invention, the porosity of the granular carrier and the effect duration time will now be described in detail with reference to the following Examples that by no means limit the scope of the present invention.

EXAMPLE 1

Figure 3:
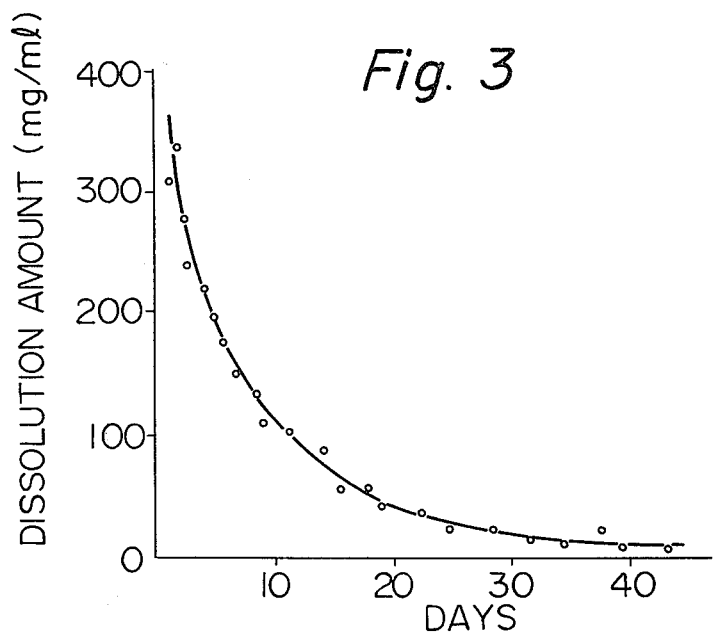
FIG. 3 is a curve illustrating the relation between the dissolution amount of a supported medicine and the lapse of time (days) in Example 1.

A small granule having a shape as shown in FIG. 2-A was formed of a porous alumina ceramic having an average pore size of 7 to 50μ and a porosity of 33%, and the average diameter of the granule was about 8 mm. An aminoglucoside antibiotic was packed in the small granule. The amount of the antibiotic dissolved out with the lapse of time at the in vitro test was plotted to obtain a dissolution curve as shown in FIG. 3. As is seen from FIG. 3, the dissolution characteristic is one represented by a curve resembling a rectangular hyperbolic curve. Accordingly, it was found that the small granule of this Example was valuable as a medicine-administering agent of a durable effect type to be used for remedy of, for example, the osteomyelitis by embedding it in the bone.

EXAMPLE 2

Figure 4:
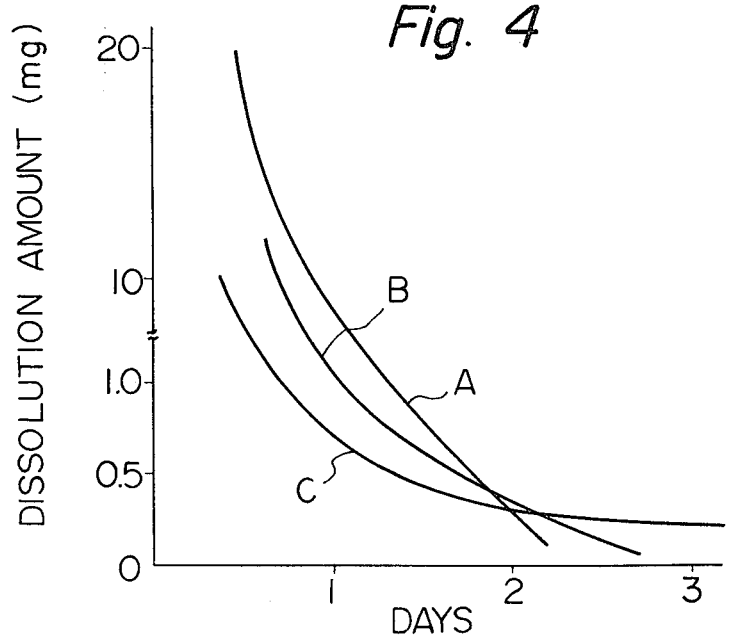
FIG. 4 is a curve illustrating the relation between the dissolution amount of a supported medicine and the lapse of time (days) in Example 2.

A small granule having a shape as shown in FIG. 1 was formed of a porous alumina ceramic material, and an antibiotic of the Cephalosporin group was supported therein and the amount of the antibiotic dissolved out with the lapse of time at the in vitro test was plotted to obtain a dissolution characteristic curve as shown in FIG. 4. More specifically, different small granules having average pore sizes and porosities shown below were used and curves A, B and C shown in FIG. 4 were obtained.

|         | Average Pore Size | Porosity |
|---------|-------------------|----------|
| Curve A | 200μ              | 35%      |
| Curve B | 30μ               | 32%      |
| Curve C | 7μ                | 29%      |

As is seen from the curve A of FIG. 4, the larger are the average pore size and porosity of the small granule, the larger is the amount of the medicine that can be supported in the small granule, and in this case, therefore, the amount of the medicine dissolved out is large but since the medicine was completely dissolved out in a relatively short time, the effect duration time of the medicine tends to be shortened.

As is seen from the curve C of FIG. 4, if both the pore size and the porosity are small, although the amount of the medicine dissolved out is relatively small, the medicine can be gradually released for a relatively long time and the medicinal effect can be maintained during a long period. Accordingly, a small granule having a relatively small pore size and a relatively low porosity can be applied to remedy of not only the osteomycelitis but also other various diseases as a medicine-administering agent of the intermediate effect type.

As will be apparent from the foregoing illustration, when the porous ceramic small granule of the present invention is used as a medicine-administering agent, the effect duration time of the medicine in the living body and the speed of release of the medicine can be freely controlled by appropriately adjusting the pore size and porosity of the small granule. Moreover, the medicine supported in the small granule of the present invention can be applied by not only oral administration but also other administration methods suitable for attaining the intended medicinal effect. For example, the small granule having a medicine supported therein can be embedded in the muscle or bone or be applied to the affected part of the living body according to other administration means appropriately selected depending on the condition and kind of the disease. Therefore, the small granule of a porous ceramic material according to the present invention is very valuable for accelerating the course of convalscence in patients suffering from various diseases.

What we claim is:

1. An agent for the administration of medicines, comprising:
   a porous ceramic carrier comprising a fired granular body of α-alumina with a particle size of about 0.1 to 20 mm;
   wherein said body has communicating pores disposed therein with the average size of said pores being from about 1 to 200 microns and the porosity of said body being from about 5 to 50 percent; and
   from about 0.1 to 30 percent by weight, based on the weight of said carrier, of a medicine supported on said carrier.

2. An agent for the administration of medicines, comprising:
   a porous ceramic carrier comprising a fired granular body of apatite with a particle size of about 0.1 to 20 mm;
   wherein said body has communicating pores disosed therein with the average size of said pores being from about 1 to 200 microns and the porosity of said body being from about 5 to 50 percent; and
   from about 0.1 to 30 percent by weight, based on the weight of said carrier, of a medicine supported on said carrier.

3. A medicine-administering agent for the remedy of osteomyelitis to be embedded in an effected bone texture or in the vicinity thereof, comprising:
   a porous ceramic carrier comprising a fired granular body of α-alumina or apatite having a particle size of from about 0.1 to 20 mm;
   wherein said body has communicating pores disposed therein wherein said pores have an average size of about 1 to 200 microns and said body has a porosity of from about 5 to 50 percent; and
   from about 0.1 to 30 percent by weight, based on the weight of said carrier, of an antibiotic supported on said carrier.

* * * * *